(12) United States Patent
Hausch

(10) Patent No.: US 12,289,840 B2
(45) Date of Patent: Apr. 29, 2025

(54) HERMETIC COATING OF COMPONENTS

(71) Applicant: Heraeus Deutschland Gmbh & Co. KG, Hanau (DE)

(72) Inventor: Ulrich Hausch, Hanau (DE)

(73) Assignee: Heraeus Medevio GmbH & Co. KG, Hanau (DE)

( * ) Notice: Subject to any disclaimer, the term of this patent is extended or adjusted under 35 U.S.C. 154(b) by 1022 days.

(21) Appl. No.: 17/319,684

(22) Filed: May 13, 2021

(65) Prior Publication Data

US 2021/0360794 A1     Nov. 18, 2021

(30) Foreign Application Priority Data

May 14, 2020    (DE) .................... 10 2020 113 106.2

(51) Int. Cl.
| | |
|---|---|
| *H05K 3/28* | (2006.01) |
| *A61N 1/375* | (2006.01) |
| *H01R 13/03* | (2006.01) |
| *H01R 13/74* | (2006.01) |
| *H05K 1/18* | (2006.01) |
| *H05K 3/30* | (2006.01) |

(52) U.S. Cl.
CPC ........... *H05K 3/284* (2013.01); *A61N 1/3754* (2013.01); *H01R 13/03* (2013.01); *H01R 13/74* (2013.01); *H05K 1/181* (2013.01); *H05K 3/303* (2013.01)

(58) Field of Classification Search
CPC ........ H05K 3/284; H05K 3/303; H05K 1/181; H01R 13/03; H01R 13/74; A61N 1/3754
See application file for complete search history.

(56) References Cited

U.S. PATENT DOCUMENTS

| | | | |
|---|---|---|---|
| 8,843,215 B2 | 9/2014 | Eck et al. | |
| 9,793,522 B2 | 10/2017 | Bhardwaj et al. | |
| 9,981,250 B2 * | 5/2018 | Wille | B01J 23/40 |
| 9,996,787 B2 * | 6/2018 | Puttkammer | H05K 1/095 |
| 10,092,766 B2 | 10/2018 | Specht et al. | |
| 10,212,836 B2 | 2/2019 | Dittmer et al. | |
| 10,617,878 B2 | 4/2020 | Fischer et al. | |
| 10,617,879 B2 | 4/2020 | Schibli et al. | |
| 10,679,778 B2 | 6/2020 | Troetzschel et al. | |
| 2011/0034965 A1 | 2/2011 | Troetzschel et al. | |
| 2011/0034966 A1 | 2/2011 | Troetzschel et al. | |
| 2011/0125210 A1 | 5/2011 | Francis | |
| 2011/0186349 A1 | 8/2011 | Troetzschel et al. | |

(Continued)

FOREIGN PATENT DOCUMENTS

| | | |
|---|---|---|
| DE | 102010006837 A1 | 8/2011 |
| DE | 102010006838 A1 | 8/2011 |

(Continued)

OTHER PUBLICATIONS

CN108242427 original with translation (Year: 2018).*

(Continued)

*Primary Examiner* — Marcus E Harcum
(74) *Attorney, Agent, or Firm* — Dicke, Billig & Czaja, PLLC

(57) ABSTRACT

One aspect relates to a process for producing an electrical medical implant, comprising the following steps: a. providing an electrical feedthrough, which comprises a substrate, an electrical component, and a contact element; b. coating the electrical component with a layer.

14 Claims, 2 Drawing Sheets

(56) References Cited

U.S. PATENT DOCUMENTS

| | | |
|---|---|---|
| 2012/0193118 A1 | 8/2012 | Kempf et al. |
| 2012/0193119 A1 | 8/2012 | Kempf et al. |
| 2012/0193141 A1 | 8/2012 | Reisinger et al. |
| 2012/0194981 A1 | 8/2012 | Kempf et al. |
| 2012/0197326 A1 | 8/2012 | Pavlovic |
| 2012/0197327 A1 | 8/2012 | Specht |
| 2012/0197368 A1 | 8/2012 | Reisinger |
| 2012/0200011 A1 | 8/2012 | Pavlovic |
| 2012/0203294 A1 | 8/2012 | Troetzschel |
| 2013/0018434 A1 | 1/2013 | Zdeblick et al. |
| 2013/0020714 A1 | 1/2013 | Patti et al. |
| 2013/0033825 A1* | 2/2013 | Brooks .................. H05K 3/284 361/748 |
| 2013/0240256 A1* | 9/2013 | Von Werne ............ H05K 1/032 427/490 |
| 2013/0299233 A1 | 11/2013 | Troetzschel et al. |
| 2014/0008121 A1 | 1/2014 | Troetzschel et al. |
| 2014/0233166 A1* | 8/2014 | O'Shea .................. H05K 1/189 174/254 |
| 2014/0268526 A1* | 9/2014 | Stevens ................ H05K 3/284 428/688 |
| 2014/0368298 A1 | 12/2014 | Reisinger |
| 2015/0122875 A1 | 5/2015 | Pavlovic et al. |
| 2016/0007482 A1* | 1/2016 | Schönholz ............. B32B 5/024 428/215 |
| 2016/0041637 A1* | 2/2016 | Guard ................ G06F 3/04164 345/174 |
| 2017/0047138 A1 | 2/2017 | Specht et al. |
| 2018/0050211 A1 | 2/2018 | Hausch et al. |
| 2018/0050212 A1 | 2/2018 | Nikolaidis et al. |
| 2018/0213665 A1 | 7/2018 | Dittmer et al. |
| 2018/0318589 A1 | 11/2018 | Donelon et al. |
| 2019/0201699 A1 | 7/2019 | Dittmer et al. |

FOREIGN PATENT DOCUMENTS

| | | | |
|---|---|---|---|
| EP | 0802710 A2 * | 10/1997 | |
| EP | 3160580 A1 | 5/2017 | |
| EP | 3284515 A1 | 2/2018 | |
| EP | 3398650 A1 | 11/2018 | |
| EP | 3351290 B1 | 6/2019 | |
| FR | 2974942 A1 * | 11/2012 | ............ H01G 4/224 |
| WO | WO 2011065989 A1 | 6/2011 | |
| WO | WO 2013075797 A1 | 5/2013 | |
| WO | WO 2016131976 A1 | 8/2016 | |

OTHER PUBLICATIONS

D. Hanft, et al., An Overview of the Aerosol Deposition Method: Process Fundamentals and New Trends in Materials Applications, Journal of Ceramic Science and Technology, vol. 6, No. 3, pp. 147-182, Sep. 2015 (37 pgs).

Akedo, Jun, "Room Temperature Impact Consolidation (RTIC) of Fine Ceramic Powder by Aerosol Deposition Method and Applications to Microdevices", Journal of Thermal Spray Technology, No. 17, pp. 181-198 Jun. 2008 (18 pgs).

Gorham, "A New, Generald Synthetic Method for the Preparation of Linear Poly-p-xylylenes", Journal of Polymer Science: Part A-1, vol. 4, No. 12, 3027-3039, 1966.

* cited by examiner

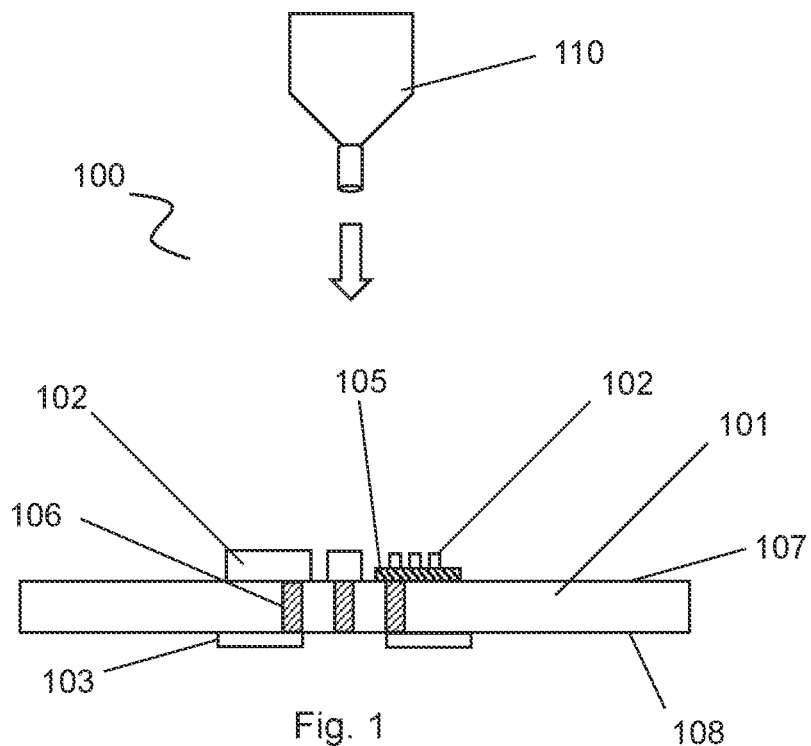
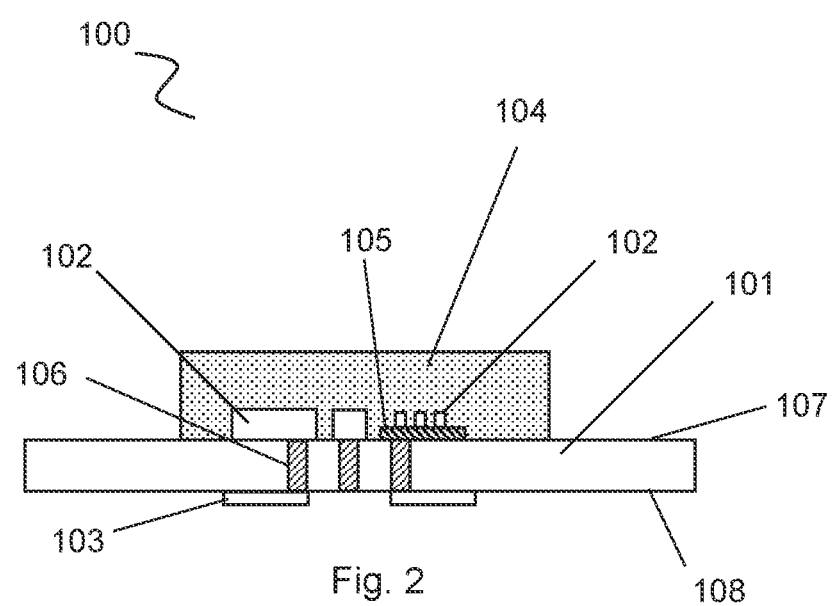

HERMETIC COATING OF COMPONENTS

CROSS-REFERENCE TO RELATED APPLICATION

This Utility Patent Application claims priority to German Application No. 102020113106.2 filed on May 14, 2020, which is incorporated herein by reference.

TECHNICAL FIELD

One aspect relates to the field of medical technology, in particular active implants, for example electrical feedthroughs for sensors and stimulators.

BACKGROUND

Active medical implants, such as, for example, pacemakers or cochlea implants, are often encapsulated in a housing made of metal. To produce such a housing, for example two housing parts made of titanium can be welded together. Such a housing part can comprise an electrical feedthrough, which provides for an electrical connection through the housing. Inside and/or outside of a housing, active medical implants usually comprise different electrical components, which have to be electrically connected to one another. In many cases, the electrical components have to be protected against contact with tissue and tissue fluid, in order to prevent damage to the components or unwanted impacts on the tissue. In particular, no tissue fluid must permeate into the housing. High demands are thus made on the tightness of electrical feedthroughs for active medical implants. Electrical feedthroughs are often installed in a housing with the help of a welding flange. The welding flange can be soldered to the housing, and the electrical feedthrough can be welded to the flange, for example by means of laser welding.

For these and other reasons there is a need for the present invention.

SUMMARY

One aspect is to solve one or several of the above-described and additional problems of the prior art. For example, one embodiment provides for an improved production process for electrical medical implants, which is simpler and more cost-efficient, for example. One embodiment furthermore provides electrical medical implants comprising an improved tightness and smaller weight.

Exemplary embodiments will be described below.
1. A process for producing an electrical medical implant, comprising the following steps:
   a. providing an electrical feedthrough, which comprises a substrate, an electrical component, and a contact element,
   b. coating the electrical component with a layer.
2. The process according to embodiment 1, wherein the coating of the electrical component takes place with the help of aerosol deposition or CVD, preferably according to the Gorham process.
3. The process according to any one of the preceding embodiments, wherein the substrate comprises a first side, which carries the electrical component, and the first side of the substrate is completely or partially coated with a layer.
4. The process according to any one of the preceding embodiments, wherein the layer is made of parylene or a ceramic material.
5. The process according to embodiment 4, wherein the ceramic material comprises $Al_2O_3$ or consists thereof.
6. The process according to any one of the preceding embodiments, wherein after the coating, the contact element is accessible for a direct electrical contacting.
7. The process according to any one of the preceding embodiments, wherein the coating takes place below a temperature of 100° C., preferably below a temperature of 50° C., more preferably at approximately 25° C.
8. The process according to any one of the preceding embodiments, wherein the coating takes place in an atmosphere with a pressure of at least 10 Pa.
9. The process according to any one of the preceding embodiments, wherein the layer has a thickness of approximately 1 µm to 10 µm, preferably 1 µm to 50 µm.
10. The process according to any one of the preceding embodiments, wherein the provision of the electrical feedthrough comprises a HTCC or LTCC process.
11. The process according to any one of the preceding embodiments, wherein the substrate comprises a ceramic material.
12. The process according to any one of the preceding embodiments, wherein the conduit element comprises a cermet.
13. The process according to any one of the preceding embodiments, wherein the coating takes place with the help of particles with an average particle size of from 10 to 100 nm.
14. The process according to any one of the preceding embodiments, wherein a further coating with metal or ceramic takes place after the coating of the component and/or substrate with the help of aerosol deposition.
15. The process according to embodiment 13, wherein the further coating takes place by means of PVD, vapor deposition, or sputtering.
16. The process according to embodiment 13 or 14, wherein the further coating creates a second layer directly on the previously applied layer.
17. The process according to any one of the preceding embodiments 14 to 16, wherein several layers of parylene, or a parylene layer and an $Al_2O_3$ layer are applied to the component, wherein the $Al_2O_3$ layer is preferably applied by means of an aerosol deposition.
18. An electrical medical implant, produced according to a process according to any one of the preceding embodiments.
19. The electrical medical implant according to embodiment 18, wherein the layer has a helium leak rate of less than $1 \times 10^{-9}$ mbar*L/s.
20. Use of a process according to any one of embodiments 1 to 18 for producing an electrical medical implant.
21. An electrical medical implant, comprising an electrical feedthrough, which comprises a substrate, an electrical component, and a contact element, wherein the electrical component is arranged on a first side of the substrate and is coated with a layer.
22. The implant according to embodiment 21, wherein the layer comprises parylene or a ceramic material, preferably $Al_2O_3$, or consists thereof.
23. The implant according to embodiment 21 or 22, wherein the electrical component is connected to the substrate directly or only via a printed circuit board.
24. The implant according to any one of embodiments 21 to 23, wherein the first side of the substrate is completely or partially coated with the layer.
25. The implant according to any one of embodiments 21 to 24, comprising a conduit element, which is arranged essentially completely within the substrate and extends from the first side of the substrate to an opposite second side of the substrate, wherein the electrical component is preferably connected to the conduit element directly or only via a printed circuit board.

26. The implant according to any one of embodiments 21 to 25, which can be implanted in the human body without housing.

27. The implant according to any one of embodiments 21 to 26, wherein the layer has a helium leak rate of less than $1\times10^{-9}$ mbar*L/s.

28. The implant according to any one of embodiments 21 to 27, wherein the layer has a thickness of approximately 1 µm to 50 µm, preferably 1 µm to 10 µm.

29. The implant according to any one of embodiments 21 to 28, wherein the conduit element comprises a cermet.

30. The implant according to any one of embodiments 21 to 29, wherein, after the coating, the contact element is accessible for a direct electrical contacting.

31. The implant according to any one of embodiments 21 to 30, wherein the contact element is not completely covered by the layer.

32. The implant according to any one of embodiments 21 to 31, wherein several layers of parylene, or a parylene layer and an $Al_2O_3$ layer are applied to the component, wherein the $Al_2O_3$ layer is preferably applied by means of an aerosol deposition.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 1 illustrates an electrical feedthrough in accordance with one embodiment.

FIG. 2 illustrates an electrical feedthrough in accordance with one embodiment.

DETAILED DESCRIPTION

Figure 3:
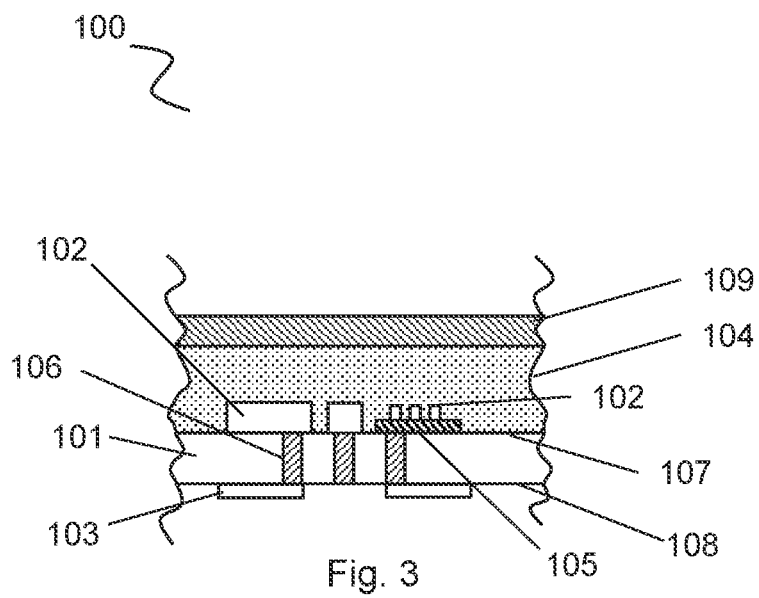
FIG. 3 illustrates a section of an electrical feedthrough with a second layer arranged on a layer.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

In addition to the embodiments described herein, the elements of which "have" or "comprise" a certain feature (e.g. a material), a further embodiment is generally always considered, in which the respective element consists solely of the feature, i.e. does not comprise any further components. The word "comprise" or "comprising" is used synonymously with the word "have" or "having" herein.

When an element is identified in the singular form in an embodiment, an embodiment is likewise contemplated in which several of these elements are present. The use of a term for an element in the plural form generally also comprises an embodiment, in which only an individual such element is present.

Unless otherwise specified or excluded unambiguously from the context, it is generally possible and is hereby unambiguously considered that features of different embodiments can also be present in the other embodiments described herein. It is likewise generally considered that all features, which are described herein in connection with a process, can also be used for the products and devices described herein, and vice versa. All of these considered combinations are not listed explicitly in all cases only in the interest of a more concise description. Technical solutions, which are obviously equivalent to the features described herein, are to generally be comprised by the scope of the invention.

One aspect of one embodiment relates to a process for producing an electrical medical implant, which comprises the following steps:

a. providing an electrical feedthrough, which comprises a substrate, an electrical component, and a contact element, b. coating the electrical component with a layer.

The layer is in one embodiment created from a vapor phase. The coating of the electrical component can take place, for example, with the help of aerosol deposition. In the alternative, the layer can also be applied, for example, with the help of CVD, for example according to the Gorham process.

In the case of CVD, also referred to as chemical vapor deposition, a solid component is deposited as layer on the surface of a substrate due to a chemical reason from the vapor phase. Volatile compounds of the layer components thereby deposit a solid layer, often at an elevated temperature of the substrate of component. The CVD process is characterized by at least one chemical reaction on the surface of the substrate or component. At least one gaseous starting compound and at least two reaction products—at least one of which in the solid phase—have to be involved in this reaction.

CVD processes, which provide for a deposition at low temperature of the surface to be coated, i.e. of the component or substrate, for example plasma enhanced chemical vapor deposition (PECVD) or HFCVD processes (hot filament CVD) are particularly preferred. The Gorham process for the deposition of parylene is an example for a particularly preferred CVD process. A group of coating materials is referred to as parylenes. In addition to the hydrocarbon poly-p-xylelene (also referred to as parylene N), halogenated derivatives thereof can be used as well. The layer is applied as closed polymer film to the component and/or substrate in a vacuum by means of resublimation from the vapor phase.

Parylene has the Structure

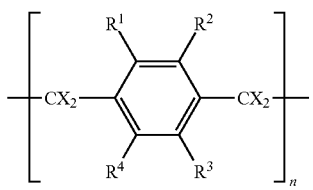

wherein R1, R2, R3, R4, and X are selected independently of one another from hydrogen or halogens. Parylene N, parylene C, parylene D, and parylene HT are preferred parylenes. The Gorham process is a frequently used process for producing parylene, and is described in GORHAM (1966), "A New, General Synthetic Process for the Preparation of Linear Poly-p-xylylenes", *J. Polym. Sci. A.* 4 (12): 3027; which is hereby incorporated by reference in its entirety.

Aerosol deposition refers to a process, in the case of which a jet of a particle material is directed at a surface of a substrate, which is to be coated. For this purpose, the particles are accelerated to a speed of, for example, 100 m/s or more, for example 200 m/s to 600 m/s, in one embodiment 300 m/s to 500 m/s with the help of a carrier gas. For example, air, nitrogen, oxygen, argon, or helium are suitable carrier gases. Any carrier gas can generally be used, which does not undergo an unwanted chemical reaction with the material of the particles or of the substrate. At first, the particles have a diameter of, for example, 200 nm to 2 µm. A plastic deformation of the particles and/or of the substrate results due to the kinetic energy of the impact, and a closed, consolidated layer thereby forms on the component from the particle material. This process is referred to as "room temperature impact consolidation". The layers formed thereby often display a very good adhesion to the component. Very even closed layers are created, which, compared to thermal spraying or screen printing, have improved properties with respect to roughness and freedom from defects. In contrast to comparable processes of the chemical vapor deposition, the aerosol deposition can be performed at normal room temperature, for example 20° C., and at higher pressures, for example 1 mbar, and provides a much higher deposition rate or higher layer thicknesses, respectively. Layer thicknesses of several micrometers can be attained within a few minutes, for example, with the help of aerosol deposition. This is particularly advantageous in the case of temperature-sensitive electrical components. The process of the aerosol deposition is described in further details, for example in J. AKEDO et al., Room Temperature Impact Consolidation (RTIC) of Fine Ceramic Powder by Aerosol Deposition Process and Applications to Microdevices, *J. Therm. Spray Tech.*, 17, 181-198 (2008); and D. HANFT et al: An Overview of the Aerosol Deposition Process: Process Fundamentals and New Trends in Materials Applications, *Journal of Ceramic Science and Technology*, 6, 147-182 (2015), which are hereby incorporated completely by reference. Depending on the used material of the particles and the surface to be coated, i.e. of the component and/or substrate, particle speed and particle size have to be selected appropriately in the individual case, in order to provide for a coating. For some materials, these parameters can be gathered from the literature and/or can be determined with simple tests, as described in the above-mentioned citations and the sources cited therein. In many cases, particle sizes of, for example, 10 to 100 nm can be used with a particle speed of from 300 to 500 m/s.

Implantable, electrical sensors, stimulators, or parts thereof, for example electrical feedthroughs, are examples for electrical medical implants. Electrical feedthroughs and further systems for electrical medical implants, in particular on the basis of cermets, are described, for example, in US2011034966A1, US2011034965A1, US2014008121A1, US2011186349A1, DE102010006837A1, DE102010006838A1, US2013299233A1, US2012197327A1, WO2013075797A1, US2017047138A1, US2012193118A1, US2012194981A1, US2012193141A1, US2015122875A1, US2012193119A1, US2012197368A1, US2014368298A1, US2012203294A1, US2012200011A1, US2012197326A1, EP3160580A1, WO2016131976A1, EP3284515A1, US2018050211A1, US2018050212A1, US2018213665A and EP3398650A1, which are hereby incorporated completely by reference.

The substrate can generally be any carrier material, which is suitable for the production of an electrical medical implant and for the reception of an electrical component. Biocompatible materials, such as, for example, a ceramic material, in particular $Al_2O_3$, or biocompatible metals or alloys, such as, for example, titanium, are preferred substrates. The ceramic material can comprise, for example, aluminum oxide ($Al_2O_3$), magnesium oxide (MgO), zirconium oxide ($ZrO_2$), aluminum nitrate ($Al_2TiO_5$), and piezoceramics, or mixtures thereof. The substrate can also comprise a metal selected from titanium (Ti), tantalum (Ta), iridium (Ir), niobium (Nb), or platinum (Pt), or an alloy of at least one of these metals.

An electrical component can be any electrical component, which can be used in an electrical medical implant. Examples for electrical components comprise integrated circuits, transistors, capacitors, coils, antennas, voltage transformers, electrical resistors, and similar components. In an embodiment according to the invention, the electrical component is a component selected from the group consisting of a data memory, a data processing unit, a power source, a recording device, and a transmitting means, or a combination of at least two of them. Any unit for storing data, which the person of skill in the art considers to be suitable for storing medical data, in one embodiment ECG data, in an implantable device, can be selected as data memory. A preferred data memory is a magnetic memory or a flash memory or both. A preferred power source is a battery or an accumulator or both. A preferred recording device is a device for recording medical data, in one embodiment cardio data, in one embodiment ECG data. A particularly preferred recording device is a biomonitor. A preferred biomonitor comprises an element selected from the group consisting of an ECG device, a Holter monitor, an event recorder, and a loop recorder, or a combination of at least two of them. A preferred ECG device is a long-term ECG device, which in one embodiment stores data accumulating over a time period of at least one hour. A preferred transmitting means is formed for a wireless, in one embodiment telemetric, transmission of data, in one embodiment ECG data. A preferred wireless transmission of data is a transmission by means of waves. Preferred waves are longitudinal waves or transversal waves or both. Preferred longitudinal waves are acoustic waves or sound waves or both. Preferred transversal waves are electromagnetic waves. Preferred electromagnetic waves are waves of the frequency of a mobile radio network or of Bluetooth or both. A preferred mobile radio network is a GSM network.

In one embodiment, the component is set up to emit an electrical signal to the human body. In one embodiment, the component is set up to receive an electrical signal from the human body. In an embodiment system, the electrical signal is associated with a physiological function. In one embodiment, the component is a functional part of a sensor or stimulator, as described herein.

A contact element is an electrically conductive element, which is set up for electrically contacting an electrical component with an electrical conductor. The contact element can be made, for example, of a metal or a metal alloy. Examples of such a contact element are described in US2013020714A1. The contact element can be, for example, a contact pad, as it is common in the semiconductor industry, for example a SMD contact pad.

In one embodiment, the substrate comprises a first side, which carries the electrical component. The first side of the substrate may be or can be completely or partially coated, respectively, with the layer. For example, only the region of the substrate, which carries the electrical component, can be coated.

The layer can be created, for example, by means of an aerosol deposition, as described herein. By controlling the particle jet, the surface of the component and/or substrate can thereby be coated by means of the raster process, also referred to as scanning, so that a location-selective coating of the component and/or substrate is possible. In one embodiment, the coating of the component and/or substrate takes place in a location-selective manner. By scanning a region several times, higher layer thickness can be attained.

In one embodiment, the first side of the substrate, which carries the electrical component, is completely or partially coated with a layer. For example, the side of the substrate bearing the electrical component may be completely or partially scanned by means of a particle jet, as described above. In the alternative or in addition, mask processes can also be used in order to shield a portion of the substrate from the particle jet. For example, particularly small structures and/or sharp dividing lines of the layer can be attained by means of a combination of scanning and masking. An only partial coating of a substrate surface can be helpful in order to keep free certain regions, for example portions of components, for the electrical contacting. The above applies analogously for the second side of the substrate opposite to the first side, whereby the second side of the substrate can likewise carry electrical components, or can comprise, for example, only contact elements. In some embodiments, an electrical lead connects the conduit element to the contact element. The electrical lead can be arranged on the second side of the substrate. It can be advantageous thereby to completely or partially coat, for example, the leads of the contact elements and/or the contact elements themselves with a layer, as described herein. In one embodiment, the contact element is accessible for a direct electrical contacting after the coating of the component and/or of the substrate.

The layer is in one embodiment an essentially closed layer of an electrically insulating material. The layer is in one embodiment essentially free from pores, holes (in particular so-called pinhole defects) and/or tears. In one embodiment, the layer is set up to insulate the component to the outside. For example, the layer protects the component against contact with air and/or human tissue. The layer can also protect the component against contact with an electrically conductive medium, for example a metal or a saline solution. The layer can thus protect the component against external influences, and can ensure an interruption-free function and long service life of the component.

The layer can, for example, be partially or completely formed from an inorganic material. In one embodiment, the layer is partially or completely formed from a ceramic material. The ceramic material can comprise, for example, aluminum oxide ($Al_2O_3$), magnesium oxide (MgO), zirconium oxide ($ZrO_2$), aluminum nitrate ($Al_2TiO_5$), and piezoceramics, or mixtures thereof.

The layer can also comprise a polymer. In one embodiment, the layer is formed from parylene. The polymer can also be applied together with an inorganic material, for example $Al_2O_3$, or can be applied in a separate process step. The polymer can be applied, for example, by using aerosol deposition or CVD, as described herein. Parylene, polyimide, or Teflon, for example, are suitable polymers. The polymer is in one embodiment a biocompatible polymer.

The processes described herein facilitate the production of electrical medical implants, which do not require a housing.

The processes described herein can facilitate the coating of temperature-sensitive components. The processes can in one embodiment be performed at low temperature. In one embodiment, the coating of the component and/or substrate takes place, for example, below a temperature of 400° C., 300° C., 200° C., or below 100° C., in one embodiment below a temperature of 50° C., the coating of the component and/or substrate in one embodiment takes place at approximately 25° C. The mentioned temperatures refer to the temperature of the component and/or substrate, whereby it is generally assumed that the component and/or substrate has the same or essentially the same temperature as the surrounding gas atmosphere.

The processes can also be performed at higher pressures than other coating processes in the prior art. A high vacuum is thus not required in order to perform the coating. The coating of the component and/or substrate can take place, for example, in an atmosphere with a pressure of at least 0.1 Pa, 1 Pa, 5 Pa, or 10 Pa. The mentioned pressure refers to the pressure within the chamber, in which the coating of the substrate takes place. The pressure is thereby optionally determined outside of the particle jet, with the largest possible distance from the particle jet.

The processes described herein provide for higher layer thicknesses than other coating processes, in particular when coating with a layer of a ceramic material. For example, a layer with a thickness of at least 100 nm, 500 nm, 1 µm, in one embodiment at least 2, 3, 4, 5, 6, 7, 8, 9, or 10 µm, or more than 20 µm, can be applied. In one embodiment, the thickness of the layer is approximately 1 µm to 10 µm.

In one embodiment, the provision of the electrical feedthrough comprises a HTCC (high temperature cofired ceramics) or LTCC (low temperature cofired ceramics) process. Examples for HTCC and LTCC processes are described in EP3351290B1, WO2011065989A1, and Barlow/Elshabini: Ceramic Interconnect Technology Handbook, CRC Press, 2007; which are hereby incorporated by reference in their entirety. In one embodiment, the provision of the electrical feedthrough comprises a lamination of several ceramic green body films. The green body films can include punched structures for receiving a metalliferous paste. By using joint sintering with the green body films, conduit elements can be produced from the metalliferous paste.

In one embodiment, the conduit element can comprise a cermet. The substrate can comprise, for example, a ceramic material, for example $Al_2O_3$, and the conduit element can comprise a cermet, wherein the cermet can comprise, for example, $Al_2O_3$. A composite material of a ceramic and a metal is referred to as "cermet". For example, a mixture of at least one ceramic powder and at least one metallic powder can be used to produce a cermet. At least one binding agent and optionally at least one solvent can be added to this mixture, in order to obtain a malleable green body. Afterwards, the binding agent and optionally the solvent are completely removed thermally and/or by using evaporation during the so-called debinding. All substances, which are mentioned as ceramic materials herein, are generally suitable substances for the ceramic contained in the cermet.

The cermet can be electrically conductive. An electrically conductive connection generally sets in in the cermet when the metal content lies above the so-called percolation threshold, at which the metal particles in the sintered cermet are connected to one another at least pointwise, so that an electrical conduction is made possible. According to experience, the metal content can for this purpose be, for example, at least 25% by volume, depending on the material selection.

The cermet can comprise a precious metal. The precious metal is in one embodiment selected from the group consisting of platinum, silver, gold, tantalum, molybdenum, and titanium.

For example, an electrical feedthrough can be produced by using the processes described herein, which comprises a conduit element, which has a cermet. For example, such a feedthrough can be produced as follows: At first, a green body film can be provided and can be provided with holes, for example by using punching. The holes can be filled with a suitable cermet paste. At this stage of the production, the cermet paste can comprise at least a mixture of metal powder, ceramic powder, and an organic vehicle. Several of the green body films filled in this way can subsequently be laminated, so that the cermet-filled holes are arranged one on top of the other. They can subsequently form the conduit element. So many filled green body films can be laminated that the desired thickness of the electrical feedthrough or length of the conduit element, respectively, is reached. During the subsequent firing, the organic vehicle can be removed at first, the cermet and the ceramic base body can be co-sintered during the subsequent transition to higher temperature. In particular a hermetically tight substance-to-substance bond between the ceramic component of the cermet and the surrounding ceramic of the base body can be created thereby.

In a further embodiment, the coating takes place with the help of particles with an average particle size of from 10 to 100 nm, 20 to 90 nm, 30 to 80 nm, or 40 to 70 nm.

In some embodiments, a further coating can take place after the coating of the component and/or substrate with the help of aerosol deposition, for example with a metal or a ceramic material. The ceramic material can in one embodiment be $Al_2O_3$. A second layer of metal can be applied, for example, to the layer applied by using the aerosol deposition method with the help of PVD, or a second layer of a ceramic material can be applied to the layer with the help of sputtering or evaporation. Aluminum is a preferred metal. The layer can also comprise a metal selected from titanium (Ti), tantalum (Ta), iridium (Ir), niobium (Nb), or platinum (Pt), or an alloy with at least one of these metals.

Due to the further coating, a layer can be created, for example, directly on the layer, which is applied by using aerosol deposition. The component is covered in this case with two different layers by using the process by using an aerosol deposition and a further coating process. It is also possible to apply two different layers one on top of the other to the component with the help of aerosol deposition. The layer can comprise, for example, $Al_2O_3$, and the second layer can comprise aluminum; or the layer can comprise parylene and the second layer can comprise aluminum. At first, the component can be coated, for example, with $Al_2O_3$ by using aerosol deposition, and an aluminum layer can be applied to the $Al_2O_3$ layer with help of a suitable process, for example PVD. In one embodiment, several layers of parylene, or a parylene layer and an $Al_2O_3$ layer can be applied to the component, whereby the $Al_2O_3$ layer is in one embodiment applied by using an aerosol deposition.

In one embodiment, a layer of parylene is at first applied to the component, and a second layer of parylene is then applied to the first parylene layer. In one embodiment, an $Al_2O_3$ layer is at first applied to the component, in one embodiment by using an aerosol deposition, and a parylene layer is then applied. In one embodiment, a parylene layer is at first applied to the component, and then a second layer of $Al_2O_3$ is applied, in one embodiment by using an aerosol deposition. In one embodiment, a parylene layer is at first applied to the component, then a second layer of $Al_2O_3$ layer is applied, and a third layer of parylene is applied thereon, wherein the $Al_2O_3$ layer is in one embodiment applied by using an aerosol deposition.

One aspect of one embodiment relates to an electrical medical implant, which can be produced or which is produced according to a process described herein. In the case of such an electrical medical implant, the layer produced according to a process described herein can have a helium leak rate of at least $1 \times 10^{-9}$ mbar*L/s.

In one embodiment, the electrically medical implant is hermetically tight. The term "hermetically tight" clarifies that moisture and/or gases cannot permeate or can only minimally permeate the hermetically tight element in the case of a proper use within the usual time periods (for example 5-10 years). A physical variable, which can describe, for example, a permeation of gases and/or moisture through a device, e.g. through the electrical feedthrough, is the so-called leak rate, which can be determined, for example, by using leak tests. Corresponding leak tests can be performed, for example, with helium leak testers and are specified in the standard Mil-STD-883G Method 1014. The maximally permissible helium leak rate is thereby specified as a function of the internal volume of the device to be tested. According to the methods specified in MIL-STD-883G, Method 1014, in paragraph 3.1, and in consideration of the volumes occurring when using the one embodiment and cavities of the devices to be tested, these maximally permissible helium leak rates can be, for example, between $1 \times 10^{-8}$ atm·cm$^3$/sec and $1 \times 10^{-7}$ atm·cm$^3$/sec. In the context of the invention, the term "hermetically tight" can in particular mean that the workpiece to be tested, in particular the layer, has a helium leak rate of less than $1 \times 10^{-7}$ atm·cm$^3$/sec. In an advantageous embodiment, the helium leak rate can be less than $10^{-8}$, $10^{-9}$, $10^{-10}$, or less than $10^{-11}$ mbar/L·s. For the purpose of the standardization, the mentioned helium leak rate can also be converted into the equivalent standard air leak rate. The definition for the equivalent standard air leak rate) and the conversion are specified in the standard ISO 3530.

The electrical medical implant can be, for example, a sensor or stimulator, or an electrical feedthrough for a sensor or stimulator.

The electrical medical implant can be a pulse generator, pacemaker, cardiac resynchronization device, sensor, or stimulator. Such devices can be used, for example, in medical applications, such as neuromodulation, cardiac stimulation, deep brain stimulation, spinal cord stimulation, or gastric stimulation. Here, a stimulator is an active implantable medical device, which can achieve a physiological effect by emitting an electrical signal to the body of a living being. A neurostimulator can affect, for example, an electrical signal in the nerve cell (e.g. an action potential) by emitting an electrical signal to a nerve cell. Pacemakers and cardioverter defibrillators are further examples for stimulators.

Here, a sensor is an implantable medical device, which can detect a physiological effect by receiving an electrical signal from the body of a living being. A cochlea implant or a retina implant is an example for a sensor.

A further aspect of one embodiment relates to the use of a process described herein for producing an electrical medical implant. The implant can be, for example, a sensor or stimulator, as described above.

A further aspect of one embodiment relates to an electrical feedthrough for an electrical medical implant, which comprises a component, which is covered with a layer.

A further aspect of one embodiment relates to an electrical medical implant, comprising an electrical feedthrough, which comprises a substrate, an electrical component, and a contact element, wherein the electrical component is arranged on a first side of the substrate and is coated with a layer.

As already mentioned, all embodiments and features, which are described above in connection with the process according to the invention, are generally used for this embodiment.

In one embodiment, the layer comprises parylene or a ceramic material, in one embodiment $Al_2O_3$, or consists thereof.

In one embodiment, the component is covered by several layers. In one embodiment, the component is covered by a parylene layer and an $Al_2O_3$ layer. In one embodiment, the component is covered by two parylene layers. In one embodiment, the component is covered by two parylene layers and an $Al_2O_3$ layer located therebetween.

In one embodiment, the electrical component is connected to the substrate directly or only via a printed circuit board.

The first side of the substrate can be completely or partially coated with the layer, as described above in connection with the process according to the invention.

The implant can comprise a conduit element, which is arranged essentially completely within the substrate and which extends from the first side of the substrate to an opposite second side of the substrate. The electrical component can thereby be connected to the conduit element directly or only via a printed circuit board. The electrical component can also be connected to the substrate directly or only via a printed circuit board. This means in particular that the electrical component is arranged directly on the substrate or at least at a very small distance from the substrate. The component can, for example, be arranged directly on the substrate in the so-called SMD design (surface mounted device). The component can also be arranged directly on a printed circuit board, which, in turn, is arranged directly on the substrate. A solder paste or a comparable connecting materials is neglected in the definition according to one embodiment for fulfilling the feature "arranged directly on", i.e. a component or a printed circuit board herein also applies as being arranged directly on the substrate when a thin layer of solder or a comparable material, which does not have a significant impact on the structural design of the implant, is located therebetween. In contrast, a component, which is connected to the substrate via a wire or a cable with a length of, for example, more than 1 mm, and which is arranged at a corresponding spatial distance from the substrate, is not arranged directly on the substrate. The above applies analogously for the direct connection of the component to the conduit element. The conduit element is in one embodiment arranged essentially completely within the substrate, i.e. it extends essentially exclusively in the region between the first side and the second side of the substrate, and serves, for example, for establishing an electrical contact between the contact element on the second side to the electrical component on the first side of the substrate.

In one embodiment, the implant can be implanted in the human body without housing. This means that the implant does not include a housing element, and can be implanted in the body with direct tissue contact without a housing, without impacting the function of the implant. "Implanted in the body" can thereby comprise the attachment of the implant to the skin, or the surgical insertion of the implant in the human body. In some embodiments, "implanted in the body" comprises the direct contact of the implant with tissue fluid in the human body. The metal layer described herein, which, as described herein, can be comprised as part of the layer according to the invention, is not understood as housing element herein. For example, a ceramic layer can be applied directly to the component, and a metal layer can be applied directly to the ceramic layer. Such a composite layer, which can have, for example, a total thickness of less than 100 µm, is not understood as "housing element" or "housing" herein.

In one embodiment, the layer of the implant has a helium leak rate of less than $1\times10^{-9}$ mbar*L/s. In one embodiment, the layer is hermetically tight, as described herein.

In one embodiment, the layer has a thickness of approximately 1 µm to 50 µm. In one embodiment, the thickness of the layer is approximately 1 µm to 10 µm. The layer can also have a thickness of more than 10 µm, for example approximately 11, 12, 15, or 20 µm, 30 µm, 40 µm, 50 µm, or more than 50 µm.

In one embodiment, the conduit element comprises a cermet, as described above in connection with the process. The cermet can comprise, for example, $Al_2O_3$ and platinum, as described above.

In one embodiment, the contact element is accessible for a direct electrical contacting after the coating. This can be attained, for example, in that the substrate is coated such that the contact element is not completely covered by the layer. This can be attained, for example, by means of location-selective coating with the help of a raster process or mask process. In one embodiment, the substrate is coated on the first side of the substrate, which carries the component, and the second side of the substrate, which carries the contact element, is not or only partially coated, so that the contact element is not completely covered by the layer.

The layer can comprise a polymer, for example a parylene, or a ceramic material, as described herein, or can consist thereof. The layer can comprise, for example, $Al_2O_3$. The layer in one embodiment has a thickness of at least 1, 2, 3, 4, 5, 6, 7, 8, 9, or 10 µm. The component can comprise a temperature-sensitive component, for example a component, which is specified for a use and/or processing at temperatures of below 300, 250, 200, 150, or below 100° C.

EXAMPLES

Embodiments will be further clarified below on the basis of examples, but which are not to be considered to be limiting. It will be clear to the person of skill in the art that, instead of the features described herein, other equivalent means can be used in a similar way.

Example 1

$Al_2O_3$ green films were sintered at a sintering temperature of 1450° C. (samples identified as "low" in Tab. 1) or 1550° C. (all other samples) for 5 hours in air, in order to produce plates of porous $Al_2O_3$ ceramic. These plates were coated with $Al_2O_3$ particles with the help of aerosol deposition and/or were coated with parylene according to the Gorham process. Before and after the coating, the plates were examined in a helium leak test. All samples were measured in 2 different orientations. The results of these measurements are displayed in Tab. 1. The first value of a sample in each case specifies the helium leak rate in orientation 1, while the respective second value of a sample specifies the helium leak rate in orientation 2. After the coating, an increased tightness compared to the uncoated control was determined in all cases. In all measurements, the helium leak rate of the uncoated ceramic plates was above the maximally measurable limit of 1×10-1 mbar*L/sec. A particularly low helium leak rate was determined in the case of a two-layer parylene coating and in the case of a combination coating with parylene and $Al_2O_3$.

TABLE 1

Results of the helium leak test.

| Sample No. | Coating | Helium leak rate [mbar*L/sec] |
|---|---|---|
| control | none | >1 × 10⁻¹ |
| 868.2 high | 10 μm parylene | 7.26 × 10⁻⁴ |
| 868.2 high | 10 μm parylene | 1.32 × 10⁻³ |
| 868.2 low | 10 μm parylene | 1.10 × 10⁻³ |
| 868.2 low | 10 μm parylene | 8.34 × 10⁻⁴ |
| 868.3 high | 10 μm parylene | 1.24 × 10⁻³ |
| 868.3 high | 10 μm parylene | 1.31 × 10⁻³ |
| 868.3 low | 10 μm parylene | 5.14 × 10⁻⁴ |
| 868.3 low | 10 μm parylene | 1.33 × 10⁻³ |
| 868.4-30026 | 1.5 μm $Al_2O_3$ | 4.01 × 10⁻² |
| 868.4-30026 | 1.5 μm $Al_2O_3$ | 6.03 × 10⁻² |
| 868.4-30025 | 1.5 μm $Al_2O_3$ | 4.14 × 10⁻² |
| 868.4-30025 | 1.5 μm $Al_2O_3$ | 6.03 × 10⁻² |
| 868.1-30028 | 3.0 μm $Al_2O_3$ | 2.29 × 10⁻² |
| 868.1-30028 | 3.0 μm $Al_2O_3$ | 5.37 × 10⁻² |
| 868.1-30027 | 3.0 μm $Al_2O_3$ | 3.71 × 10⁻² |
| 868.1-30027 | 3.0 μm $Al_2O_3$ | 6.03 × 10⁻² |
| 868.1 | 3 μm $Al_2O_3$ + 10 μm parylene | 4.23 × 10⁻⁷ |
| 868.4 | 3 μm $Al_2O_3$ + 10 μm parylene | 1 × 10⁻¹¹ |
| 868.3 high | 10 μm parylene + 10 μm parylene | 5.23 × 10⁻⁹ |
| 868.3 low | 10 μm parylene + 10 μm parylene | 4.36 × 10⁻⁹ |

FIG. 1 illustrates an electrical feedthrough 100 in an exemplary manner, which can be coated with the help of the process described herein. The electrical feedthrough 100 comprises a substrate 101, which can have a ceramic material. Electrical components 102 are arranged on the substrate 101 on a first side 107. The electrical components 102 can either be connected directly to the substrate 101, as illustrated in the left part of the drawing, or they can be connected to the substrate 101 via a printed circuit board 105, as illustrated in the right part of the drawing. In the latter case, one or several electrical components 102 can be arranged on a printed circuit board 105, which is connected to the substrate 101 directly or indirectly. The feedthrough 100 furthermore comprises one or several conduit elements 106, wherein a conduit element 106 is in electrical communication with an electrical component 102. For example, several components 102 can be arranged on the first side 107 of the substrate 101. Components 102 can also be arranged on an opposite second side 108 of the substrate 101. The electrical feedthrough 100 comprises a contact element 103, which is arranged in electrical communication with a conduit element 106. For example, a component 102 and a contact element 103 are arranged on respective opposite sides 107 and 108 of the substrate 101, and are connected to one another via a conduit element 106. A first side 107 of the substrate 101 and/or a component 102 can be coated with the help of a particle source 110. For this purpose, the particle source 110 directs a particle jet at a surface of the substrate 101 and/or of the component 102. The direction of the particle jet is illustrated in FIG. 1 by means of an arrow. The particle jet is directed at the substrate 101 in such a way that an electrical component 102 is covered with a layer 104.

FIG. 2 illustrates an electrical feedthrough 100 according to the invention, in the case of which several components 102 are completely covered by a layer 104. The individual elements can be arranged as described in FIG. 1. The layer 104 surrounds the components 102 in such a way that they are protected completely against contact with the external air and/or human tissue. The use of an outer housing can be forgone thereby. The feedthrough 100 can thus be implanted directly in the human body without an additional housing.

FIG. 3 illustrates a section of an electrical feedthrough 100, in the case of which a second layer 109 is arranged on the layer 104. For example, the layer 104 can comprise parylene, and the second layer 109 can comprise $Al_2O_3$, or vice versa. The layer 104 and the layer 109 can also comprise the same material, for example $Al_2O_3$ or parylene. The second layer 109 can completely cover the first layer 104, so that the first layer 104 is protected against contact with the external atmosphere.

Figure 4:
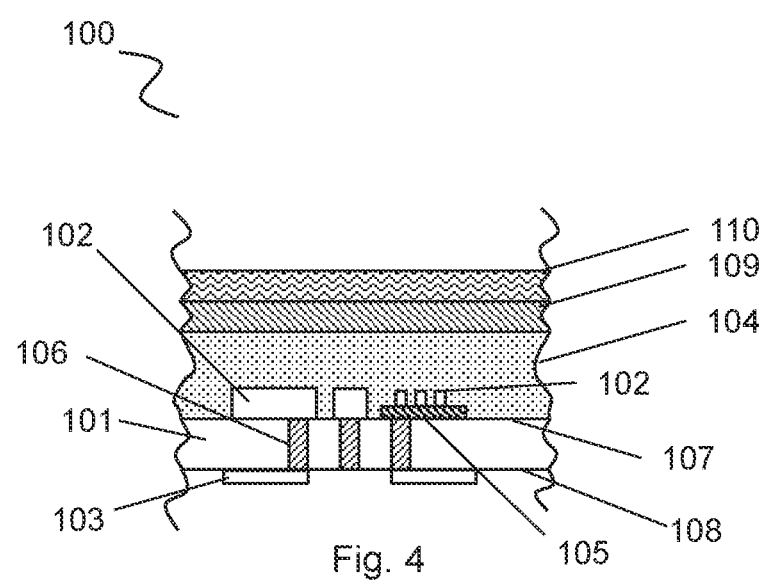
FIG. 4 illustrates a section of an electrical feedthrough with a third layer arranged on the second layer.

FIG. 4 illustrates a section of an electrical feedthrough 100, in the case of which a third layer 110 is arranged on the second layer 109. For example, the layer 104 can comprise parylene, the second layer 109 can comprise $Al_2O_3$, and the third layer 110 can likewise comprise parylene. The third layer 110 can completely cover the second layer 109, so that the second layer 109 is protected against contact with the external atmosphere.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

The invention claimed is:

1. A process for producing an electrical medical implant, comprising:
    providing an electrical feedthrough comprising a substrate, an electrical component, and a contact element;
    arranging a conduit element within the substrate and extending from a first side of the substrate to an opposite second side of the substrate; and
    coating the electrical component with a parylene layer and an $Al_2O_3$ layer;

wherein the conduit element comprises a cermet; and
wherein the produced implant is configured to be implanted in the human body without a housing.

2. The process according to claim 1, wherein the coating of the electrical component is done with aerosol deposition or CVD.

3. The process according to claim 1, wherein the coating of the electrical component is done with a Gorham process.

4. The process according to claim 1, wherein the coating takes place below a temperature of 100° C.

5. The process according to claim 1, wherein the coating takes place at approximately 25° C.

6. The process according to claim 1, wherein the coating takes place in an atmosphere with a pressure of at least 10 Pa.

7. The process according to claim 1, wherein the substrate comprises a ceramic material.

8. An electrical medical implant, comprising:
an electrical feedthrough, which comprises a substrate;
a conduit element, which is arranged within the substrate and extends from a first side of the substrate to an opposite second side of the substrate, wherein the conduit element comprises a cermet;
an electrical component; and
a contact element, wherein the electrical component is arranged on the first side of the substrate and is coated with a parylene layer and an $Al_2O_3$ layer;
wherein the implant is configured to be implanted in the human body without a housing.

9. The implant according to claim 8, wherein the electrical component is connected to the substrate directly or only via a printed circuit board.

10. The implant according to claim 8, comprising the conduit element, which is arranged essentially completely within the substrate and extends from the first side of the substrate to an opposite second side of the substrate, wherein the electrical component is connected to the conduit element directly or only via a printed circuit board.

11. The implant according to of claim 8, wherein the layer has a helium leak rate of less than $1\times10^{-9}$ mbar*L/s.

12. The implant according to claim 8, wherein the layer has a thickness of approximately 1 μm to 50 μm.

13. The implant according to claim 8, wherein the layer has a thickness of approximately 1 μm to 10 μm.

14. The implant according to claim 8, wherein, after the coating, the contact element is accessible for a direct electrical contacting.

* * * * *